(12) United States Patent
Huber

(10) Patent No.: US 6,346,542 B1
(45) Date of Patent: Feb. 12, 2002

(54) PESTICIDAL COMPOSITION COMPRISING ENANTIOMERIC FORM OF FIPRONIL

(75) Inventor: Scot Kevin Huber, Raleigh, NC (US)

(73) Assignee: Aventis CropScience S.A., Lyons (FR)

( * ) Notice: Subject to any disclaimer, the term of this patent is extended or adjusted under 35 U.S.C. 154(b) by 0 days.

(21) Appl. No.: 09/550,312

(22) Filed: Apr. 14, 2000

Related U.S. Application Data

(60) Provisional application No. 60/129,371, filed on Apr. 15, 1999, and provisional application No. 60/139,892, filed on Jun. 22, 1999.

(51) Int. Cl.[7] ............... A01N 43/56; A61K 31/415; C07D 231/44
(52) U.S. Cl. ............... 514/404; 548/367.4
(58) Field of Search ............ 548/367.4; 514/404

(56) References Cited

U.S. PATENT DOCUMENTS

| 5,232,940 A | 8/1993 | Hatton et al. |
| 6,057,355 A | 5/2000 | Haas et al. ............... 514/404 |

FOREIGN PATENT DOCUMENTS

| EP | 0295117 | 12/1988 |

*Primary Examiner*—Robert W. Ramsuer
(74) *Attorney, Agent, or Firm*—Burns, Doane, Swecker & Mathis, L.L.P.

(57) ABSTRACT

A composition comprising (S)-5-amino-3-cyano-1-(2,6-dichloro-4-trifluoromethylphenyl)-4-trifluoromethylsulfinylpyrazole and (R)-5-amino-3-cyano-1-(2,6-dichloro-4-trifluoromethylphenyl)-4-trifluoromethylsulfinylpyrazole, enantiomerically enriched in the (S)-enantiomer.

71 Claims, No Drawings

PESTICIDAL COMPOSITION COMPRISING ENANTIOMERIC FORM OF FIPRONIL

CROSS-REFERENCE TO RELATED APPLICATIONS

This application claims the priority of U.S. Provisional Patent Applications No. 60/129,371, filed Apr. 15, 1999, and Ser. No. 60/139,892, filed Jun. 22, 1999, both incorporated by reference herein in their entireties and relied upon.

BACKGROUND OF THE INVENTION

1. Field of the Invention

The present invention relates to a new composition comprising pesticidal compounds having a chiral center, which chiral center cooperates with an adjacent amino group.

Although chirality usually arises from the presence of a carbon atom to which four different atoms or groups are attached, other atoms, including sulphur, can also give rise to chiral centers.

2. Background Art

It is known from, inter alia, EP-A-0 295 117 and Hatton et al U.S. Pat. No. 5,232,940, that certain N-phenylpyrazole compounds are useful for the control of arthropod, plant nematode, helminth and protozoan pests. These compounds include N-phenylpyrazoles having an optionally substituted amino group attached to the 5-position. Such substituted amino groups include amino substituted by one or two groups selected from alkyl and alkanoyl. Compounds of interest include those having a cyano group attached to the 3-position and a group $RS(O)_n$ attached to the 4-position, R being selected from alkyl and haloalkyl and n being 0, 1 or 2. When the group $RS(O)_n$ represents a sulfoxide, RS(O), the resulting compounds are generally chiral compounds which exist as a mixture of two enantiomers (also known as enantiomeric isomers).

Among the compounds in the above-mentioned publications is listed 5-amino-3-cyano-1-(2,6-dichloro-4-trifluoromethylphenyl)-4-trifluoromethylsulfinylpyrazole, which is depicted as the following formula (A):

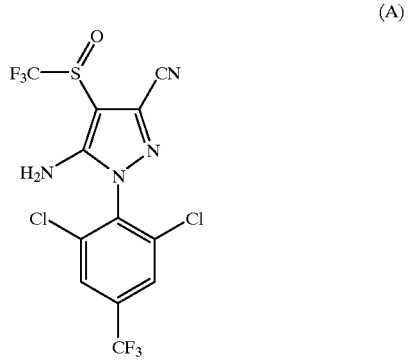

(A)

This compound is presently used commercially to control pests in, for example, agriculture, public health and animal health, and is known as fipronil.

SUMMARY AND OBJECTS OF THE INVENTION

The compound of formula (A), although it does not contain any chiral carbon atoms, is a racemic mixture of enantiomers by virtue of the —S(O)CF$_3$ group. The existence of the enantiomers has not been previously disclosed. The known racemic mixture causes emesis in animals to which it is administered orally.

It is desirable in the control of arthropod pests on animals for compounds to be orally administered. Investigation of the class of N-phenylpyrazoles having an optionally substituted amino group attached to the 5-position of the pyrazole ring has now shown that the level of emetic effect of such oral administration is influenced by a combination of parameters: the presence or absence of substitution on the 5-position; the nature of the substitution; and the chirality of the sulfoxide group on the 4-position.

Placement of an acetyl group on the 5-amino group in formula (A) causes a dramatic increase in toxicity and emesis. At a dose of 10 mg/kg in dogs, both enantiomers have caused emesis in about two-thirds of the animals. However, the (S) enantiomer has caused 100% mortality in testing whereas the (R) enantiomer has caused 33% mortality. Although monosubstitution on the 5-amino group by acetyl causes an increase in emetic activity and mortality, it has been discovered that addition of a methyl substituent on the amino group and replacement of acetyl by ethoxyacetyl or tetrahydrofur-2-oyl can reduce both emetic activity and mortality.

Such chemical modification of the 5-amino group can, however, be avoided by separation of the compound of formula (A) into its component (R) and (S) enantiomers. In contrast to the 5-acetylamino enantiomers [where the (S) enantiomer has caused 100% mortality], it is the (S) enantiomer of the 5-amino compound which is the better of the two enantiomers in that it has lower emetic activity. The (S) enantiomer of the 5-amino compound also possesses a second advantageous property. Improved long term control of ticks can be obtained by its use. For example, at a dose of 10 mg/kg administered orally to dogs, the (S) enantiomer at 23 days after administration has been found 85% effective, compared to only 71% effectiveness for the (R) enantiomer (corresponding to only 15% of ticks remaining instead of 29%).

An object of the present invention is to provide a composition comprising 5-amino-3-cyano-1-(2,6-dichloro-4-trifluoromethylphenyl)-4-trifluoromethylsulfinylpyrazole which is substantially enriched in an enantiomer.

Another object of the invention is to provide a composition which is generally safer to use in veterinary medicine or agriculture or public health.

Another object of the invention is to provide a composition which when administered orally to animals is substantially non-emetic, most preferably when about 70% or more of the animals so treated are free of emesis.

These objects are met in whole or in part by the present invention. The present invention provides a composition comprising (S)-5-amino-3-cyano-1-(2,6-dichloro-4-trifluoromethylphenyl)-4-trifluoromethylsulfinylpyrazole and (R)-5-amino-3-cyano-1-(2,6-dichloro-4-trifluoromethylphenyl)-4-trifluoromethylsulfinylpyrazole wherein the composition is enriched in the (S) enantiomer.

DETAILED DESCRIPTION OF THE INVENTION AND PREFERRED EMBODIMENTS

By the term "non-emetic" is meant a composition that does not generally elicit emesis from an animal when a protective, preventative or cleaning dose is administered to said animal. By the term "substantially non-emetic" is meant that, generally, when a composition of the invention is administered to a population of animals, more than 70% (or at least ⅔) of the animals are free of emesis. Preferably, more than 80%, most preferably more than 90%, of said population is free of emesis.

By the term "enriched" is meant wherein the (S):(R) weight:weight ratio is at least approximately 1.05 or higher. Preferably, the composition of the invention is substantially enriched in the (S) enantiomer. By the term "substantially enriched" is meant wherein the (S):(R) weight: weight ratio is at least approximately 1.5 or higher.

In a further aspect of the invention, the (S):(R) weight-:weight ratio is at least approximately 2 or greater, preferably at least approximately 5 or greater, most preferably at least approximately 10 or greater.

For greater clarity, the structures of (S)-5-amino-3-cyano-1-(2,6-dichloro-4-trifluoromethylphenyl)-4-trifluoromethylsulfinylpyrazole and (R)-5-amino-3-cyano-1-(2,6-dichloro-4-trifluoromethylphenyl)-4-trifluoromethylsulfinylpyrazole are depicted below as formulas (B) and (C), respectively. The optical configurations of formulas (B) and (C) are assigned by the use of the Cahn-Ingold-Prelog system as generally described in *Advanced Organic Chemistry*, J. March, 3$^{rd}$ edition, pp. 96–97, Wiley Interscience, NY, 1985. Such depictions are generally understood by those skilled in the art.

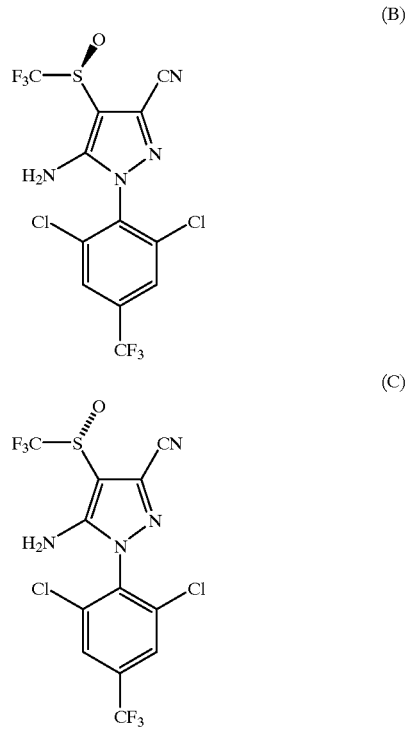

The composition of the invention may further comprise a carrier for use in veterinary medicine, animal health, agriculture, or public health. Such compositions as generally described in EP-A-0 295 117 and Hatton et al U.S. Pat. No. 5,232,940, but comprising the (S) and (R) enantiomers substantially enriched in one enantiomer [preferably enriched in the (S) enantiomer], in a pesticidally effective amount (in place of the known racemic mixture), together with a carrier, preferably in a substantially non-emetic amount, are useful herein. See Hatton et al U.S. Pat. No. 5,232,940, incorporated by reference herein in its entirety and relied upon.

The present invention also provides a method of controlling pests at a locus which method comprises applying a composition according to the present invention in a pesticidally effective amount at the locus, preferably in an amount which is also substantially non-emetic.

Compound A may be prepared according to the methods described in EP-A-0 295 117 and Hatton et al U.S. Pat. No. 5,232,940.

In one aspect of the invention, the composition may be prepared by separating the enantiomers of fipronil in whole or in part by, for example, use of column chromatography or reverse-phase column chromatography using a substantially optically active (or "chiral") stationary phase as known to those skilled in the art.

In another aspect of the invention, the enantiomers may be separated by a process which comprises:

(a) reacting compound (A) with a compound (EF) wherein:
   E is an organic radical which is enantiomerically enriched, for example, substantially enantiomerically pure, and F is a group reactive with amino, for example a carboxylic acid, carboxylic acid anhydride, carboxylic acid halide or a carboxylic acid derivative suitable for use in the reaction as known to the skilled addressee; to provide the compounds of formula (III-A) and formula (III-B) (which are novel and therefore constitute a feature of the invention)

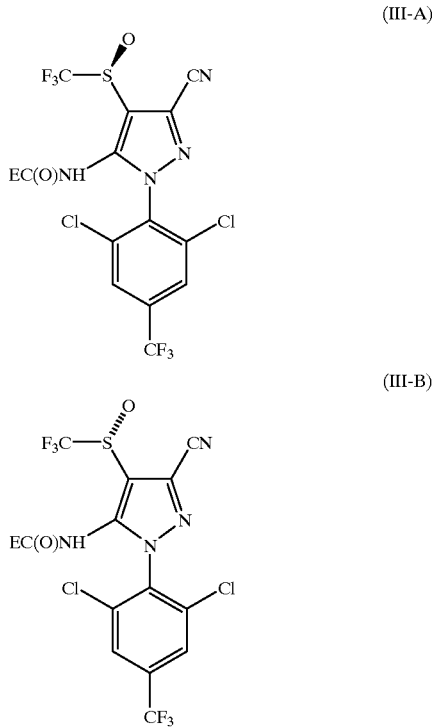

(b) separating the compounds of formulas (III-A) and (III-B); and (c) removing the groups EC(O) of compounds of formula (III-A) and/or (III-B), for example, by hydrolysis to separately provide (S)-5-amino-3-cyano-1-(2,6-dichloro-4-trifluoromethylphenyl)-4-trifluoromethylsulfinylpyrazole and/or (R)-5-amino-3-cyano-1-(2,6-dichloro-4-trifluoromethylphenyl)-4-trifluoromethylsulfinylpyrazole, respectively.

The products of step (a), that is the compounds of formula (III-A) and (III-B), are two diastereomers which may be separated by use of, for example, column chromatography or reverse-phase column chromatography as known to those skilled in the art.

The reactant EF can be, for example, a Moscher acid halide, an Evans chiral auxiliary activated for reaction, a sugar moiety suitably activated for reaction or an amino acid suitably protected and activated for reaction.

When the radical E comprises a primary amine, secondary amine or tertiary amine, the products of step (a), that is the compounds of formulas (III-A) and (III-B), are two diastereomers which may be converted to the corresponding acid addition salts, and then separated, for example, by use of fractional crystallization as known to those skilled in the art.

When the radical E comprises a carboxylic acid, sulfonic acid or other such acidic moiety, the products of step (a), that is the compounds of formulas (III-A) and (III-B), are two diastereomers which may be converted to the corresponding salts which may be separated by, for example, use of fractional crystallization as known to those skilled in the art.

In step (c), the removal of the amide generally comprises a chemical hydrolysis as known to those skilled in the art.

In a preferred aspect of the present invention, there is provided the (S) enantiomer of fipronil, i.e. (S)-5-amino-3-cyano-1-(2,6-dichloro-4-trifluoromethylphenyl)-4-trifluoromethylsulfinylpyrazole, substantially free of (R) enantiomer. By "substantially free of (R) enantiomer" is meant that less than about 5% (R) enantiomer is present, i.e., the (S):(R) ratio by weight is at least 95:5. Preferably, the (S):(R) ratio by weight is at least 98:2, that is, less than about 2% (R) enantiomer is present; more preferably, the (S):(R) ratio by weight is at least 99:1, that is, less than about 1% of (R) enantiomer is present.

In another aspect of the invention, there is provided the isolated compound (S)-5-amino-3-cyano-1-(2,6-dichloro-4-trifluoromethylphenyl)-4-trifluoromethylsulfinylpyrazole.

In another aspect of the invention, the composition of the invention may be prepared by a selective oxidation of 5-amino-3-cyano-1-(2,6-dichloro-4-trifluoromethylphenyl)-4-trifluoromethylthiopyrazole to preferentially provide the (S) enantiomer. Such oxidation methods are known to those skilled in the art of organic synthesis. It is also possible to utilize such separation methods as for example hereinbefore described, to recover the (R) enantiomer of fipronil and convert it by a reduction/oxidation scheme to produce the (S) enantiomer.

It has been unexpectedly found that (S)-5-amino-3-cyano-1-(2,6-dichloro-4-trifluoromethylphenyl)-4-trifluoromethylsulfinylpyrazole provides a substantial advantage in the control of certain arthropods at an animal locus. Another unexpected substantial advantage is that the (S) enantiomer provides a substantial reduction in emesis when administered to an animal orally. By the term "emesis" is meant vomiting. Generally, an emetic substance elicits emesis in less than 24 hours after administration, usually less than 8 hours, more usually less than 2 hours.

The present invention also relates to a use of the composition as hereinbefore defined for the manufacture of a veterinary composition for the control of arthropod parasites in or on an animal.

The present invention also relates to a method of cleaning animals in good health comprising the application to the animal of the composition as hereinbefore defined.

The method of cleaning an animal is not a method of treatment by therapy of the animal body per se, because:

(a) the animal is in good health and requires no substantial treatment to correct a deficiency of health;

(b) the cleaning of the animal is not intended to be done by veterinary personnel, but by persons interested in the cleaning of the animal; and (c) the purpose of such cleaning is to avoid unpleasant conditions for humans and the environment which humans inhabit so as to not infest the humans with arthropods carried by the animal.

The present invention also provides the use of a composition as described supra as an active veterinary substance.

The compositions which may be used according to the invention generally comprise from about 0.001% to 99% of active ingredient. The remainder of the composition up to 100% comprises a carrier as well as generally various additives. In this specification and the accompanying claims, percentages are by weight unless otherwise indicated.

The diluted liquid formulations generally comprise from about 0.001% to about 20% of active ingredient, preferably from about 0.1% to about 3%. Solid formulations generally comprise from about 10% to 99% of active ingredient, preferably from about 40% to 70%.

Compositions for oral administration comprise the active ingredient in association with pharmaceutically acceptable carriers or coatings and include, for example, tablets, pills, capsules, gels, drenches, medicated feeds, medicated drinking water, medicated dietary supplements, slow-release boluses or other slow-release devices intended to be retained within the gastro-intestinal tract. Any of these may incorporate the active ingredients contained within microcapsules or coated with acid-labile or alkali-labile or other pharmaceutically acceptable enteric coatings. Feed premixes or concentrates containing compounds of the present invention for use in preparation of medicated diets, drinking water or other materials for consumption by animals may also be used.

According to the present invention the active ingredient (ai) is administered orally in a dose to an animal in a dose range generally from 0.1mg/kg to 500 mg/kg of ai per kilogram of animal body weight (mg/kg), more preferably from 1 mg/kg to 100 mg/kg, even more preferably from 1 mg/kg to 50 mg/kg, and most preferably from 1 mg/kg to 20 mg/kg.

Examples of the pests that may be controlled by the active ingredient are generally described in European Patent Application EP-A-0 295 117 and Hatton et al U.S. Pat. No. 5,232,940, incorporated by reference herein in its entirety and relied upon. Illustrative of specific parasites of various host animals which may be controlled by the present invention include arthropods such as mites (e.g., mesostigmatids, itch, mange, scabies, chiggers), ticks (e.g., soft-bodied and hard-bodied), lice (e.g., sucking, biting), fleas (e.g., dog flea, cat flea, oriental rat flea, human flea), true bugs (e.g., bed bugs, Triatomid bugs), bloodsucking adult flies (e.g., horn fly, horse fly, stable fly, black fly, deer fly, louse fly, tsetse fly, mosquitoes), and parasitic fly maggots (e.g, bot fly, blow fly, screwworn, cattle grub, fleeceworm); helminths such as nematodes (e.g., threadworm, lungworm, hookworm, whipworm, nodular worm, stomach worm, round worm, pinworm, heartworm), cestodes (e.g., tapeworms) and trematodes (e.g., liver fluke, blood fluke); protozoa such as coccidia, trypanosomes, trichomonads, amoebas and plasmodia; acanthocephalans such as thorny-headed worms (e.g., lingulatulida); and pentastomids such as tongueworms. Arthropod pests that are particularly well controlled by the present invention are fleas and ticks.

It will be understood that by the term "animals" is meant mammals, preferably domestic animals, e.g., pets, or commercial animals, that is, animals intended to produce a commercial product such as leather or wool, e.g., cows, sheep and horses; and mammals in captivity such as zebras, lions or bears. It will be understood that by the term "pets" is meant, for example, dogs or cats.

Another aspect of the present invention is the use of the compound (R)-fipronil as an emetic substance in the field of pest control where an emetic effect is desired, for example to act as a protection means in order to increase the safety of the use. Generally, the use of (R)-fipronil is at the same rates as those indicated here above for (S)-fipronil and the compositions containing this (R)-fipronil have the same forms, ratios and components as those described hereinabove for (S)-fipronil; it is also possible to adjust the use rates and forms to maximize the emetic effect.

The following examples provide non-limiting methods to work the invention.

EXAMPLE 1

About 120 mg of fipronil, i.e., a 1:1 mixture by weight of (S)-5-amino-3-cyano-1-(2,6-dichloro-4-trifluoromethylphenyl)-4-trifluoromethylsulfinylpyrazole and (R)-5-amino-3-cyano-1-(2,6-dichloro-4-trifluoromethylphenyl)-4-trifluoromethylsulfinylpyrazole, were separated by HPLC (high-pressure liquid chromatography) using a stationary phase which was a Chiralcel® OD 21 mm×250 mm column, particle size about 20 microns (micrometers) and a mobile phase of isooctane: isopropanol 96:6 v/v ratio to provide 60 mg each of each enantiomer. The elution rate was about 6 mL per minute. Compound C, the (R) enantiomer, came off the column after about 20 minutes and Compound B, the (S) enantiomer, came off the column after about 40 minutes.

Solvent was removed from both samples and white powders were obtained.

The melting point of Compound B was about 204° C. and the melting point of Compound C was about 201° C.

The absolute configurations of the enantiomers as shown in formulas B and C were determined by recrystallizations of both substances from isopropanol and subsequent analysis by single crystal X-ray diffraction.

EXAMPLE 2

Each of the compounds B and C of EXAMPLE 1 were formulated as a capsule in gelatin and orally administered to 10 mixed breed dogs at a rate of 20 mg of the compound per kg of body weight of the animal treated.

All animals were infested with cat fleas (*Ctenocephalides felis*) and brown dog ticks (*Rhipicephalus sanguineus*) 1 day prior to administration of the compounds. Counts of arthropods were made 1 day after treatment (DAT). Immediately after the determination of efficacy, all arthropods were removed from the dogs. The animals were re-infested with arthiropods at 8, 15, 22, and 30 days after treatment and efficacy determinations were made at 9, 16, 23, and 31 days after treatment.

The following efficacy results were obtained in per cent (%) mortality of the arthropods.

| DAT | Compound B Flea | Compound B Tick | Compound C Flea | Compound C Tick |
| --- | --- | --- | --- | --- |
| 1 | 100 | 99 | 100 | 97 |
| 9 | 96 | 97 | 86 | 96 |
| 16 | 86 | 87 | 69 | 85 |
| 23 | 88 | 86 | 67 | 77 |
| 31 | 84 | 92 | 69 | 81 |

Within 5 hours after administration of the compounds, 50% of the dogs treated with the (S) enantiomer showed emesis whereas 90% of the dogs treated with the (R) enantiomer showed emesis.

EXAMPLE 3

The test of EXAMPLE 2 was repeated at the levels indicated and the following results were obtained:

| | Compound B | | | | | | Compound C | | | | | |
| --- | --- | --- | --- | --- | --- | --- | --- | --- | --- | --- | --- | --- |
| | 1 mg/kg | | 3 mg/kg | | 10 mg/kg | | 1 mg/kg | | 3 mg/kg | | 10 mg/kg | |
| DAT | Flea | Tick | Flea | Tick | Flea | Tick | Flea | Tick | Flea | Tick | Flea | Tick |
| 1 | 100 | 100 | 100 | 98 | 100 | 99 | 100 | 100 | 100 | 93 | 100 | 97 |
| 9 | 100 | 100 | 98 | 99 | 99 | 100 | 100 | 100 | 78 | 89 | 95 | 97 |
| 16 | 90 | 87 | 67 | 75 | 87 | 85 | 76 | 66 | 72 | 71 | 72 | 71 |
| 23 | 79 | 85 | 50 | 63 | 83 | 85 | 72 | 78 | 64 | 65 | 86 | 71 |

At the 1 mg/kg treatment level, neither compound showed emesis in the animals.

At the 3 mg/kg treatment level, 20% of the animals treated with Compound C [the (R) enantiomer] showed emesis symptoms after 2 hours.

At the 10 mg/kg treatment level, 40% of the animals treated with Compound C [the (R) enantiomer] showed emesis symptoms after 1 hour. After 3 hours, 20% of the animals treated with the Compound C [the (R) enantiomer] showed emesis symptoms.

There were substantially no symptoms of emesis in animals treated with Compound B [the (S) enantiomer] at any rate.

While the invention has been described in terms of various preferred embodiments, the person skilled in the art will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. A composition comprising (S)-5-amino-3-cyano-1-(2,6-dichloro-4-trifluoromethylphenyl)-4-trifluoromethylsulfinylpyrazole and (R)-5-amino-3-cyano-1-(2,6-dichloro-4-trifluoromethylphenyl)-4-trifluoromethylsulfinylpyrazole, enriched in the (S) enantiomer.

2. A composition according to claim 1, substantially enriched in the (S) enantiomer.

3. A composition according to claim 1, wherein the (S):(R) weight:weight ratio is at least 2.

4. A composition according to claim 1, wherein the (S):(R) weight:weight ratio is at least 5.

5. A composition according to claim 1, wherein the (S):(R) weight:weight ratio is at least 10.

6. A composition according claim 1, further comprising a pesticidally acceptable carrier.

7. A composition according to claim 1, formulated for use in veterinary medicine.

8. A composition according to claim 2, formulated for use in veterinary medicine.

9. A composition according to claim 3, formulated for use in veterinary medicine.

10. A composition according to claim 4, formulated for use in veterinary medicine.

11. A composition according to claim 5, formulated for use in veterinary medicine.

12. A composition according to claim 7, in oral dosage form.

13. A composition according to claim 8, in oral dosage form.

14. A composition according to claim 9, in oral dosage form.

15. A composition according to claim 10, in oral dosage form.

16. A composition according to claim 11, in oral dosage form.

17. A composition according to claim 1, formulated for use in agriculture.

18. A composition according to claim 1, formulated for use in public health.

19. A method for controlling pests at a locus, said method comprising applying to said locus a pesticidally effective amount of a composition comprising (S)-5-amino-3-cyano-1-(2,6-dichloro-4-trifluoromethylphenyl)-4-trifluoromethylsulfinylpyrazole and (R)-5-amino-3-cyano-1-(2,6-dichloro-4-trifluoromethylphenyl)-4-trifluoromethylsulfinylpyrazole, enriched in the (S) enantiomer.

20. A method according to claim 19, wherein the composition is substantially enriched in the (S) enantiomer.

21. A method according to claim 19, wherein the (S):(R) weight:weight ratio is at least 2.

22. A method according to claim 19, wherein the (S):(R) weight:weight ratio is at least 5.

23. A method according to claim 19, wherein the (S):(R) weight:weight ratio is at least 10.

24. A method according to claim 19, wherein the composition further comprises a pesticidally acceptable carrier.

25. A method according to claim 19, wherein the locus is an animal.

26. A method according to claim 20, wherein the locus is an animal.

27. A method according to claim 21, wherein the locus is an animal.

28. A method according to claim 22, wherein the locus is an animal.

29. A method according to claim 23, wherein the locus is an animal.

30. A method according to claim 25, wherein the composition is orally administered to the animal.

31. A method according to claim 26, wherein the composition is orally administered to the animal.

32. A method according to claim 27, wherein the composition is orally administered to the animal.

33. A method according to claim 28, wherein the composition is orally administered to the animal.

34. A method according to claim 29, wherein the composition is orally administered to the animal.

35. A method according to claim 30, wherein the animal is a cat or dog.

36. A method according to claim 31, wherein the animal is a cat or dog.

37. A method according to claim 32, wherein the animal is a cat or dog.

38. A method according to claim 33, wherein the animal is a cat or dog.

39. A method according to claim 34, wherein the animal is a cat or dog.

40. The compound (S)-5-amino-3-cyano-1-(2,6-dichloro-4-trifluoromethylphenyl)-4-trifluoromethylsulfinylpyrazole, substantially free of the (R) enantiomer.

41. The compound according to claim 40, at least 98% free of the (R) enantiomer.

42. The compound according to claim 41, at least 99% free of the (R) enantiomer.

43. The isolated compound (S)-5-amino-3-cyano-1-(2,6-dichloro-4-trifluoromethylphenyl)-4-trifluoromethylsulfinylpyrazole.

44. A pesticidal composition comprising a pesticidally effective amount of the compound according to claim 40 and a pesticidally acceptable carrier therefor.

45. A pesticidal composition comprising a pesticidally effective amount of the compound according to claim 41 and a pesticidally acceptable carrier therefor.

46. A pesticidal composition comprising a pesticidally effective amount of the compound according to claim 42 and a pesticidally acceptable carrier therefor.

47. A pesticidal composition comprising a pesticidally effective amount of the compound according to claim 43 and a pesticidally effective carrier therefor.

48. A pesticidal composition according to claim 44, formulated for use in veterinary medicine.

49. A pesticidal composition according to claim 45, formulated for use in veterinary medicine.

50. A pesticidal composition according to claim 46, formulated for use in veterinary medicine.

51. A pesticidal composition according to claim 47, formulated for use in veterinary medicine.

52. A pesticidal composition according to claim 48, in oral dosage form.

53. A pesticidal composition according to claim 49, in oral dosage form.

54. A pesticidal composition according to claim 50, in oral dosage form.

55. A pesticidal composition according to claim 51, in oral dosage form.

56. A method for controlling pests at a locus, said method comprising applying to said locus a pesticidally effective amount of the compound according to claim 40.

57. A method for controlling pests at a locus, said method comprising applying to said locus a pesticidally effective amount of the compound according to claim 43.

58. A method for controlling pests at a locus, said method comprising applying to said locus a pesticidally effective amount of a composition according to claim 44.

59. A method for controlling pests at a locus, said method comprising applying to said locus a pesticidally effective amount of a composition according to claim 47.

60. A method according to claim 56, wherein the locus is an animal.

61. A method according to claim 57, wherein the locus is an animal.

62. A method according to claim 58, wherein the locus is an animal.

63. A method according to claim 59, wherein the locus is an animal.

64. A method according to claim 60, wherein the compound is orally administered to the animal.

65. A method according to claim 61, wherein the compound is orally administered to the animal.

66. A method according to claim 62, wherein the composition is orally administered to the animal.

67. A method according to claim 63, wherein the composition is orally administered to the animal.

68. A method according to claim 64, wherein the animal is a cat or dog.

69. A method according to claim 65, wherein the animal is a cat or dog.

70. A method according to claim 66, wherein the animal is a cat or dog.

71. A method according to claim 67, wherein the animal is a cat or dog.

* * * * *